(12) United States Patent
Buhr et al.

(10) Patent No.: US 7,314,935 B2
(45) Date of Patent: Jan. 1, 2008

(54) TRICYCLIC N-ACYL COMPOUNDS

(75) Inventors: Wilm Buhr, Konstanz (DE); Jörg Senn-Bilfinger, Konstanz (DE); Peter Jan Zimmerman, Radolfzell (DE); Peter Zimmerman, Konstanz (DE)

(73) Assignee: Altana Pharma AG, Konstanz (DE)

( * ) Notice: Subject to any disclaimer, the term of this patent is extended or adjusted under 35 U.S.C. 154(b) by 79 days.

(21) Appl. No.: 10/504,432

(22) PCT Filed: Feb. 12, 2003

(86) PCT No.: PCT/EP03/01349

§ 371 (c)(1),
(2), (4) Date: Aug. 13, 2004

(87) PCT Pub. No.: WO03/068774

PCT Pub. Date: Aug. 21, 2003

(65) Prior Publication Data

US 2005/0148618 A1    Jul. 7, 2005

(30) Foreign Application Priority Data

Feb. 15, 2002    (EP) .................... 02003536

(51) Int. Cl.
*C07D 471/06*    (2006.01)
*A61K 31/437*    (2006.01)

(52) U.S. Cl. ........................ 546/82; 514/293

(58) Field of Classification Search .......... 546/82; 514/293

See application file for complete search history.

(56) References Cited

U.S. PATENT DOCUMENTS 6,384,048 B1 *   5/2002   Senn-Bilfinger ............ 514/293

FOREIGN PATENT DOCUMENTS

| WO | 98/42707 A1 | 10/1998 |
|----|-------------|---------|
| WO | 00/17200 A1 | 3/2000 |
| WO | 00/26217 A1 | 5/2000 |
| WO | 00/63211 A1 | 10/2000 |
| WO | 01/72754 A1 | 10/2001 |
| WO | 01/72756 A1 | 10/2001 |
| WO | 01/72757 A1 | 10/2001 |
| WO | 02/34749 A1 | 5/2002 |
| WO | WO03/014119 | * 2/2003 |

* cited by examiner

*Primary Examiner*—Rita Desai
(74) *Attorney, Agent, or Firm*—The Nath Law Group; Joshua B. Goldberg; Sheldon M. McGee

(57) ABSTRACT

The invention relates to compounds of the formula (1) where the substituents and symbols are as defined in the description. The compounds are valuable intermediates for preparing active pharmaceutical ingredients.

4 Claims, No Drawings

TRICYCLIC N-ACYL COMPOUNDS

TECHNICAL FIELD

The invention relates to novel compounds which are used in the pharmaceutical industry as valuable intermediates for preparing active ingredients.

PRIOR ART

The International Patent Applications WO 98/42707, WO 00/17200, WO 00/26217, WO 00/63211, WO 01/72756, WO 01/72754, WO 01/72757 and WO 02/34749 disclose tricyclic imidazopyridine derivatives having very particular substitution patterns which are said to be suitable for treating gastric and intestinal diseases.

DESCRIPTION OF THE INVENTION

The invention provides compounds of the formula 1

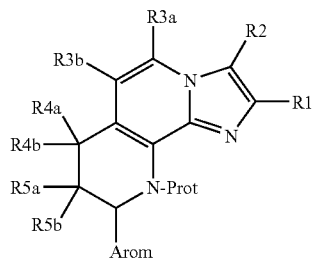

(1)

where

R1 is hydrogen, $C_{1-4}$-alkyl, $C_{3-7}$-cycloalkyl, $C_{3-7}$-cycloalkyl-$C_{1-4}$-alkyl, $C_{1-4}$-alkoxy, $C_{1-4}$-alkoxy-$C_{1-4}$-alkyl, $C_{1-4}$-alkoxycarbonyl, $C_{2-4}$-alkenyl, $C_{2-4}$-alkynyl, fluoro-$C_{1-4}$-alkyl or hydroxy-$C_{1-4}$-alkyl, R2 is hydrogen, $C_{1-4}$-alkyl, $C_{3-7}$-cycloalkyl, $C_{3-7}$-cycloalkyl-$C_{1-4}$-alkyl, $C_{1-4}$-alkoxycarbonyl, hydroxy-$C_{1-4}$-alkyl, halogen, $C_{2-4}$-alkenyl, $C_{2-4}$-alkynyl, fluoro-$C_{1-4}$-alkyl or cyanomethyl, R3a is hydrogen, halogen, fluoro-$C_{1-4}$-alkyl, $C_{1-4}$-alkyl, $C_{2-4}$-alkenyl, $C_{2-4}$-alkynyl, $C_{1-4}$-alkoxy, carboxyl, $C_{1-4}$-alkoxycarbonyl, hydroxy-$C_{1-4}$-alkyl, $C_{1-4}$-alkoxy-$C_{1-4}$-alkyl, $C_{1-4}$-alkoxy-$C_{1-4}$-alkoxy-$C_{1-4}$-alkyl, fluoro-$C_{1-4}$-alkoxy-$C_{1-4}$-alkyl or the —CO—NR31R32 radical, R3b is hydrogen, halogen, fluoro-$C_{1-4}$-alkyl, $C_{1-4}$-alkyl, $C_{2-4}$-alkenyl, $C_{2-4}$-alkynyl, $C_{1-4}$-alkoxy, carboxyl, $C_{1-4}$-alkoxycarbonyl, hydroxy-$C_{1-4}$-alkyl, $C_{1-4}$-alkoxy-$C_{1-4}$-alkyl, $C_{1-4}$-alkoxy-$C_{1-4}$-alkoxy-$C_{1-4}$-alkyl, fluoro-$C_{1-4}$-alkoxy-$C_{1-4}$-alkyl or the —CO-NR31R32 radical, where R31 is hydrogen, $C_{1-7}$-alkyl, hydroxy-$C_{1-4}$-alkyl or $C_{1-4}$-alkoxy-$C_{1-4}$-alkyl and R32 is hydrogen, $C_{1-7}$-alkyl, hydroxy-$C_{1-4}$-alkyl or $C_{1-4}$-alkoxy-$C_{1-4}$-alkyl, or where R31 and R32 together, including the nitrogen atom to which they are both bonded, are a pyrrolidino, piperidino or morpholino radical, R4a is hydrogen or R41-O, R5a is hydrogen, and R4b and R5b together are a bond, where R41 Is a suitable oxygen protecting group, or where R4a is hydroxyl, and R5a, R4b and R5b are each hydrogen, Arom is a mono- or bicyclic aromatic radical which is substituted by R6, R7, R8 and R9 and is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R6 is hydrogen, $C_{1-4}$-alkyl, hydroxy-$C_{1-4}$-alkyl, $C_{1-4}$-alkoxy, $C_{2-4}$-alkenyloxy, $C_{1-4}$-alkylcarbonyl, carboxyl, $C_{1-4}$-alkoxycarbonyl, carboxy-$C_{1-4}$-alkyl, $C_{1-4}$-alkoxycarbonyl-$C_{1-4}$-alkyl, halogen, hydroxyl, aryl, aryl-$C_{1-4}$-alkyl, aryloxy, aryl-$C_{1-4}$-alkoxy, trifluoromethyl, nitro, amino, mono- or di-$C_{1-4}$-alkylamino, $C_{1-4}$-alkylcarbonylamino, $C_{1-4}$-alkoxycarbonylamino, $C_{1-4}$-alkoxy-$C_{1-4}$-alkoxycarbonylamino or sulphonyl, R7 is hydrogen, $C_{1-4}$-alkyl, $C_{1-4}$-alkoxy, $C_{1-4}$-alkoxycarbonyl, halogen, trifluoromethyl or hydroxyl, R8 is hydrogen, $C_{1-4}$-alkyl or halogen and R9 is hydrogen, $C_{1-4}$-alkyl or halogen, where aryl is phenyl or substituted phenyl having one, two or three identical or different substituents from the group of $C_{1-4}$-alkyl, $C_{1-4}$-alkoxy, carboxyl, $C_{1-4}$-alkoxycarbonyl, halogen, trifluoromethyl, nitro, trifluoromethoxy, hydroxyl and cyano, Prot is an amino protecting group, and their salts.

$C_{1-4}$-Alkyl represents straight-chain or branched alkyl radicals having 1 to 4 carbon atoms. Examples include the butyl, iso-butyl, sec-butyl, tert-butyl, propyl, isopropyl, ethyl and methyl radicals.

$C_{3-7}$-Cycloalkyl represents cyclopropyl, cyclobutyl, cyclopentyl, cyclohexyl and cycloheptyl, of which preference is given to cyclopropyl, cyclobutyl and cyclopentyl.

$C_{3-7}$-Cycloalkyl-$C_{1-4}$-alkyl represents one of the abovementioned $C_{1-4}$-alkyl radicals which is substituted by one of the abovementioned $C_{3-7}$-cycloalkyl radicals. Examples include the cyclopropylmethyl, cyclo-hexylmethyl and cyclohexylethyl radicals.

$C_{1-4}$-Alkoxy represents radicals which, in addition to the oxygen atom, contain a straight-chain or branched alkyl radical having 1 to 4 carbon atoms. Examples include the butoxy, iso-butoxy, sec-butoxy, tert-butoxy, propoxy, isopropoxy and preferably the ethoxy and methoxy radicals.

$C_{1-4}$-Alkoxy-$C_{1-4}$-alkyl represents one of the abovementioned $C_{1-4}$-alkyl radicals which is substituted by one of the abovementioned $C_{1-4}$-alkoxy radicals. Examples include the methoxymethyl, methoxyethyl and butoxyethyl radicals.

$C_{1-4}$-Alkoxycarbonyl (—CO—$C_{1-4}$-alkoxy) represents a carbonyl group to which one of the abovementioned $C_{1-4}$-alkoxy radicals is bonded. Examples include the methoxycarbonyl ($CH_3O$—$C(O)$—) and ethoxycarbonyl ($CH_3CH_2O$—$C(O)$—) radicals.

$C_{2-4}$-Alkenyl represents straight-chain or branched alkenyl radicals having 2 to 4 carbon atoms. Examples include the 2-butenyl, 3-butenyl, 1-propenyl and 2-propenyl (allyl) radicals.

$C_{2-4}$-Alkynyl represents straight-chain or branched alkynyl radicals having 2 to 4 carbon atoms. Examples include the 2-butynyl, 3-butynyl and preferably the 2-propynyl (propargyl) radicals.

Fluoro-$C_{1-4}$-alkyl represents one of the abovementioned $C_{1-4}$-alkyl radicals which is substituted by one or more fluorine atoms. An example is the trifluoromethyl radical.

Hydroxy-$C_{1-4}$-alkyl represents the abovementioned $C_{1-4}$-alkyl radicals which are substituted by a hydroxyl group. Examples include the hydroxymethyl, 2-hydroxyethyl and 3-hydroxypropyl radicals.

For the purposes of the invention, halogen is bromine, chlorine and fluorine.

$C_{1-4}$-Alkoxy-$C_{1-4}$-alkoxy represents one of the abovementioned $C_{1-4}$-alkoxy radicals which is substituted by a further $C_{1-4}$-alkoxy radical. Examples include the 2-(methoxy)ethoxy ($CH_3$—O—$CH_2$—$CH_2$—O—) and 2-(ethoxy)ethoxy ($CH_3$—$CH_2$—O—$CH_2$—$CH_2$—O—) radicals.

$C_{1-4}$-Alkoxy-$C_{1-4}$-alkoxy-$C_{1-4}$-alkyl represents one of the abovementioned $C_{1-4}$-alkoxy-$C_{1-4}$-alkyl radicals which is substituted by one of the abovementioned $C_{1-4}$-alkoxy radicals. An example is the 2-(methoxy)ethoxymethyl ($CH_3$—O—$CH_2$—$CH_2$—O—$CH_2$—) radical.

Fluoro-$C_{1-4}$-alkoxy-$C_{1-4}$-alkyl represents one of the abovementioned $C_{1-4}$-alkyl radicals which is substituted by a fluoro-$C_{1-4}$-alkoxy radical. Fluoro-$C_{1-4}$-alkoxy represents one of the abovementioned $C_{1-4}$-alkoxy radicals which is predominantly or fully substituted by fluorine. Examples of predominantly or fully fluorine-substituted $C_{1-4}$-alkoxy include the 1,1,1,3,3,3-hexafluoro-2-propoxy, 2-trifluoromethyl-2-propoxy, 1,1,1-trifluoro-2-propoxy, perfluoro-tert-butoxy, 2,2,3,3,4,4,4-heptafluoro-1-butoxy, 4,4,4-trifluoro-1-butoxy, 2,2,3,3,3-pentafluorpropoxy, perfluoroethoxy or 1,2,2-trifluoroethoxy radicals, in particular the 1,1,2,2-tetrafluoroethoxy, 2,2,2-trifluoroethoxy or trifluoromethoxy radicals, and preferably the difluoromethoxy radical.

$C_{1-7}$-Alkyl represents straight-chain or branched alkyl radicals having 1 to 7 carbon atoms. Examples include the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

$C_{2-4}$-Alkenyloxy represents a radical which, In addition to the oxygen atom, contains a $C_{2-4}$-alkenyl radical. An example is the allyloxy radical.

$C_{1-4}$-Alkylcarbonyl represents a radical which, in addition to the carbonyl group, contains one of the abovementioned $C_{1-4}$-alkyl radicals. An example is the acetyl radical.

An example of carboxy-$C_{1-4}$-alkyl is the carboxymethyl (—$CH_2COOH$) or the carboxyethyl (—$CH_2CH_2COOH$) radical.

$C_{1-4}$-Alkoxycarbonyl-$C_{1-4}$-alkyl represents one of the abovementioned $C_{1-4}$-alkyl radicals which is substituted by one of the abovementioned $C_{1-4}$-alkoxycarbonyl radicals. An example is the ethoxy-carbonylmethyl radical ($CH_3CH_2OC(O)CH_2$—).

Aryl-$C_{1-4}$-alkyl represents an aryl-substituted $C_{1-4}$-alkyl radical. An example is the benzyl radical.

Aryl-$C_{1-4}$-alkoxy represents an aryl-substituted $C_{1-4}$-alkoxy radical. An example is the benzyloxy radical.

In addition to the nitrogen atom, mono- or di-$C_{1-4}$-alkylamino radicals contain one or two of the abovementioned $C_{1-4}$-alkyl radicals. Preference is given to di-$C_{1-4}$-alkylamino and in particular dimethyl-, diethyl- or diisopropylamino.

$C_{1-4}$-Alkylcarbonylamino represents an amino group to which is bonded a $C_{1-4}$-alkylcarbonyl radical. Examples include the propionylamino ($C_3H_7C(O)NH$—) and the acetylamino (acetamido) ($CH_3C(O)NH$—) radicals.

$C_{1-4}$-Alkoxycarbonylamino represents an amino radical which is substituted by one of the above-mentioned $C_{1-4}$-alkoxycarbonyl radicals. Examples include the ethoxycarbonylamino and methoxycarbonylamino radicals.

$C_{1-4}$-Alkoxy-$C_{1-4}$-alkoxycarbonyl represents a carbonyl group which is bonded to one of the above-mentioned $C_{1-4}$-alkoxy-$C_{1-4}$-alkoxy radicals. Examples include the 2-(methoxy)ethoxycarbonyl ($CH_3$—O—$CH_2CH_2$—O—CO—) and the 2-(ethoxy)ethoxycarbonyl ($CH_3CH_2$—O—$CH_2CH_2$—O—CO—) radicals.

$C_{1-4}$-Alkoxy-$C_{1-4}$-alkoxycarbonylamino represents an amino radical which is substituted by one of the abovementioned $C_{1-4}$-alkoxy-$C_{1-4}$-alkoxycarbonyl radicals. Examples include the 2-(methoxy)ethoxycarbonylamino and 2-(ethoxy)ethoxycarbonylamino radicals.

Useful oxygen protecting groups R41 are in principle any groups which behave in the desired manner on further conversion of the compounds of the formula 1, i.e., for example, can be converted by oxidation with suitable oxidizing agents to a keto group and by reduction with suitable reducing agents to a hydroxyl group. Examples of protecting groups include the $C_{1-4}$-alkoxycarbonyl, $C_{1-4}$-alkoxy-$C_{1-4}$-alkoxycarbonyl and $C_{1-4}$-alkylcarbonyl radicals. In a preferred embodiment of the invention, the R41 and Prot groups are identical.

Examples of Arom radicals include the following substituents: 4-acetoxyphenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3-methoxyphenyl, 3,5-bis(trifluoromethyl)phenyl, 4-butoxyphenyl, 2-chlorophenyl, 3-chlorophenyl, 4-chlorophenyl, 2-chloro-6-fluorophenyl, 3-chloro-4-fluorophenyl, 2-chloro-5-nitrophenyl, 4-chloro-3-nitrophenyl, 3-(4-chlorophenoxy)phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy-4-hydroxyphenyl, 2-fluorophenyl, 4-fluorophenyl, 4-hydroxyphenyl, 2-hydroxy-5-nitrophenyl, 3-methoxy-2-nitrophenyl, 3-nitrophenyl, 2,3,5-trichlorophenyl, 2,4,6-trihydroxyphenyl, 2,3,4-trimethoxyphenyl, 2-hydroxy-1-naphthyl, 2-methoxy-1-naphthyl, 4-methoxy-1-naphthyl, 1-methyl-2-pyrrolyl, 2-pyrrolyl, 3-methyl-2-pyrrolyl, 3,4-dimethyl-2-pyrrolyl, 4-(2-methoxycarbonylethyl)-3-methyl-2-pyrrolyl, 5-ethoxycarbonyl-2,4-dimethyl-3-pyrrolyl, 3,4-dibromo-5-methyl-2-pyrrolyl, 2,5-dimethyl-1-phenyl-3-pyrrolyl, 5-carboxy-3-ethyl-4-methyl-2-pyrrolyl, 3,5-dimethyl-2-pyrrolyl, 2,5-dimethyl-1-(4-trifluoromethylphenyl)-3-pyrrolyl, 1-(2,6-dichloro-4-trifluoromethylphenyl)-2-pyrrolyl, 1-(2-nitrobenzyl)-2-pyrrolyl, 1-(2-fluorophenyl)-2-pyrrolyl, 1-(4-trifluoromethoxyphenyl)-2-pyrrolyl, 1-(2-nitrobenzyl)-2-pyrrolyl, 1-(4-ethoxycarbonyl)-2,5-dimethyl-3-pyrrolyl, 5-chloro-1,3-dimethyl-4-pyrazolyl, 5-chloro-1-methyl-3-trifluormethyl-4-pyrazolyl, 1-(4-chlorobenzyl)-5-pyrazolyl, 1,3-dimethyl-5-(4-chlorophenoxy)-4-pyrazolyl, 1-methyl-3-trifluoromethyl-5-(3-trifluoromethylphenoxy-4-pyrazolyl, 4-methoxycarbonyl-1-(2,6-dichlorophenyl)-5-pyrazolyl, 5-allyloxy-1-methyl-3-trifluoromethyl-4-pyrazolyl, 5-chloro-1-phenyl-3-trifluoromethyl-4-pyrazolyl, 3,5-dimethyl-1-phenyl-4-imidazolyl, 4-bromo-1-methyl-5-imidazolyl, 2-butylimidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-3-indolyl, 6-benzyloxy-3-indolyl, 2-methyl-5-nitro-3-indolyl, 4,5,6,7-tetrafluoro-3-indolyl, 1-(3,5-difluorobenzyl)-3-indolyl, 1-methyl-2-(4-trifluorophenoxy)-3-indolyl, 1-methyl-2-benzimidazolyl, 5-nitro-2-furyl, 5-hydroxymethyl-2-furyl, 2-furyl, 3-furyl, 5-(2-nitro-4-trifluoromethylphenyl)-2-furyl, 4-ethoxycarbonyl-5-methyl-2-furyl, 5-(2-trifluoromethoxyphenyl)-2-furyl, 5-(4-methoxy-2-nitrophenyl)-2-furyl, 4-bromo-2-furyl, 5-dimethylamino-2-furyl, 5-bromo-2-furyl, 5-sulpho-2-furyl, 2-benzofuryl, 2-thienyl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2-thienyl, 3-phenoxy-2-thienyl, 5-carboxy-2-thienyl, 2,5-dichloro-3-thienyl, 3-methoxy-2-thienyl, 2-benzothienyl, 3-methyl-2-benzothienyl, 2-bromo-5-chloro-3-benzothienyl, 2-thiazolyl, 2-amino-4-chloro-5-thiazolyl, 2,4-dichloro-5-thiazolyl, 2-diethylamino-5-thiazolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6-dichloro-4-pyridyl, 3-chloro-5-trifluoromethyl-2-pyridyl, 4,6-dimethyl-2-pyridyl, 4-(4-chlorophenyl)-3-pyridyl, 2-chloro-5-methoxycarbonyl-6-methyl-4-phenyl-3-pyridyl, 2-chloro-3-pyridyl, 6-(3-trifluoromethylphenoxy)-3-pyridyl, 2-(4-chlorophenoxy)-3-pyridyl, 2,4-dimethoxy-5-pyrimidine, 2-quinolinyl, 3-quinolinyl, 4quinolinyl, 2-chloro-3-quinolinyl, 2-chloro-6-methoxy-3-quinolinyl, 8-hydroxy-2-quinolinyl and 4-isoquinolinyl.

Useful amino protecting groups are in principle any protecting groups used for protecting amino acids in peptide and protein syntheses or for protecting other amines, for example in alkaloid or nucleotide syntheses (on this subject, see, for example, T. W. Greene and P. G. M. Wuts, Protective groups In organic synthesis, 2nd edition, 1991, John Wiley & Sons, Inc., pages 309-385). Examples of useful protecting groups include the $C_{1-4}$-alkylcarbonyl (for example acetyl), $Cl_{4}$-alkoxycarbonyl (for example butoxycarbonyl), $C_{1-4}$-alkoxy-$C_{1-4}$-alkoxycarbonyl, benzyloxycarbonyl or nitrobenzenesulphenyl radicals. Preference is given to the acetyl radical.

Useful salts for compounds of the formula 1, depending on the substitution, are in particular all acid addition salts. Particular mention is made of the salts of the customarily used inorganic and organic acids. Useful salts are the water-soluble and water-insoluble acid addition salts with the acids, for example hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, and, depending on whether the acid is mono- or polybasic and depending on which salt is desired, the acids in the salt preparation are used in an equimolar ratio or a ratio deviating therefrom.

It is known to those skilled in the art that both the compounds according to the invention and their salts, when, for example, they are isolated in crystalline form, may contain different amounts of solvents. The invention therefore also encompasses all solvates and in particular all hydrates of the compounds of the formula 1, and also all solvates and in particular all hydrates of the salts of the compounds of the formula 1.

There are in principle three chiral centres in the basic skeleton of the compounds of the formula 1. The invention therefore provides all conceivable stereoisomers in any desired mixing ratio to one another, including the pure enantiomers which are provided with preference by the invention.

Compounds to be emphasized are those of the formula 1 where

R1 is hydrogen, $C_{1-4}$-alkyl, $C_{3-7}$-cycloalkyl, $C_{1-4}$-alkoxy-$C_{1-4}$-alkyl, $C_{2-4}$-alkynyl or fluoro-$C_{1-4}$-alkyl, R2 Is hydrogen, $C_{1-4}$-alkyl, halogen, $C_{2-4}$-alkenyl, $C_{2-4}$-alkynyl or fluoro-$C_{1-4}$-alkyl, R3a is hydrogen, R3b is hydrogen, halogen, $C_{1-4}$-alkyl or the —CO—NR31R32 radical,
  where
  R31 is hydrogen, $C_{1-7}$-alkyl, hydroxy-$C_{1-4}$-alkyl or $C_{1-4}$-alkoxy-$C_{1-4}$-alkyl and
  R32 Is hydrogen, $C_{1-7}$-alkyl, hydroxy-$C_{1-4}$-alkyl or $C_{1-4}$-alkoxy-$C_{1-4}$-alkyl,
  or where
  R31 and R32 together, including the nitrogen atom to which they are both bonded, are a pyrrolidino, piperidino or morpholino radical, R4a is hydrogen or R41-O, R5a is hydrogen, and R4b and R5b together are a bond, where
R41 is a suitable oxygen protecting group,
or where
R4a is hydroxyl, and R5a, R4b and R5b are each hydrogen,
Arom is a mono- or bicyclic aromatic radical which is substituted by R6, R7, R8 and R9 and is selected from the group consisting of phenyl, furanyl (furyl) and thiophenyl (thienyl),
  where
  R6 is hydrogen, $C_{1-4}$-alkyl, hydroxy-$C_{1-4}$-alkyl, $C_{1-4}$-alkoxy, $C_{1-4}$-alkylcarbonyl, carboxyl, $C_{1-4}$-alkoxycarbonyl, halogen, hydroxyl, trifluoromethyl, $C_{1-4}$-alkylcarbonylamino, $C_{1-4}$-alkoxycarbonylamino, $C_{1-4}$-alkoxy-$C_{1-4}$-alkoxycarbonylamino or sulphonyl,
  R7 is hydrogen, $C_{1-4}$-alkyl, $C_{1-4}$-alkoxy, $C_{1-4}$-alkoxycarbonyl, halogen, trifluoromethyl or hydroxyl,
  R8 is hydrogen and
  R9 is hydrogen,
Prot is an amino protecting group, and their salts.

Among the compounds according to the invention, emphasis is given to the optically pure compounds of the formula 1*

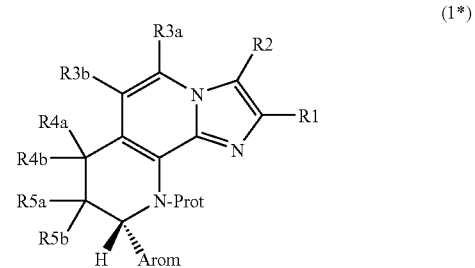

(1*)

and their salts.

Particular emphasis is given to compounds of the formula 1* where
R1 is hydrogen, methyl, cyclopropyl, methoxymethyl or trifluoromethyl,
R2 is hydrogen, methyl, chlorine, bromine, ethynyl or trifluoromethyl,
R3a is hydrogen,
R3b is hydrogen, fluorine, methyl or the —CO—N(CH$_3$)$_2$ radical, R4a is hydrogen or R41-O, R5a is hydrogen, and R4b and R5b together are a bond, where
R41 is a suitable oxygen protecting group,
or where
R4a is hydroxyl, and R5a, R4b and R5b are each hydrogen,
Arom is a phenyl radical and
Prot is an amino protecting group, and their salts.

Preference is given to compounds of the formula 1*
where
R1 is methyl,
R2 is methyl,
R3a is hydrogen,
R3b is hydrogen,
R4a is hydrogen or R41-O, R5a is hydrogen, and R4b and R5b together are a bond, where
R41 is a suitable oxygen protecting group,
or where
R4a is hydroxyl and R5a, R4b and R5b are each hydrogen,
Arom is a phenyl radical and
Prot is an amino protecting group, and their salts.

The compounds of the formula 1 according to the invention where R1, R2, R3a, R3b, Arom and Prot are each as defined above, and R4a is R41-O, R5a is hydrogen and R4b and R5b together are a bond may be prepared from the compounds of the formula 2

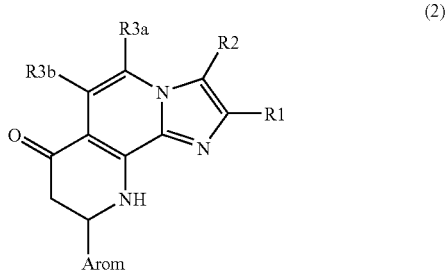

(2)

by introducing the protecting groups R41 and Prot in a suitable manner. The way in which the protecting groups are introduced depends on their type and is familiar to those skilled in the art on the basis of their knowledge. In a preferred embodiment of the invention, the R41 and Prot groups are identical, so that these groups can be introduced at the same time in one reaction step. When R41 and Prot are each an acetyl group, the reaction of compounds of the formula 2 may be carried out, for example, with acetyl chloride, or preferably with acetic anhydride under suitable conditions.

The compounds of the formula 1 according to the invention where R1, R2, R3a, R3b, Arom and Prot are each as defined above, and R4a is hydroxyl and R5a, R4b and R5b are each hydrogen may be prepared from the compounds of the formula 1 in which R4a is R41-O, R5a is hydrogen, and R4b and R5b together are a bond, where R41 is a suitable oxygen protecting group, by reduction with a suitable reducing agent. An example of a suitable reducing agent is sodium borohydride.

The compounds of the formula 1 according to the invention where R1, R2, R3a, R3b, Arom and Prot are each as defined above, and R4a and R5a are each hydrogen, and R4b and R5b together are a bond may be prepared from the compounds of the formula 1 in which R4a is hydroxyl, and R5a, R4b and R5b are each hydrogen, by elimination (dehydration) in a manner known per se, preferably under acid catalysis and/or using a suitable dehydrating agent (see, for example, Patai-Rappaport, The Chemistry of the Hydroxyl Group, Vol. 2, pp. 641-718, New York, Wiley 1971).

The compounds of the formula 1 according to the invention are valuable precursors and intermediates for preparing tetrahydroimidazo[1,2-h][1,7]naphthyridines, as described, for example, in the International Patent Applications WO 98/42707, WO 00/17200, WO 00/26217, WO 00/63211, WO 01/72756, WO 01/72754, WO 01/72757 and WO 02/34749. Exemplary conversions of compounds of the formula 1 to the abovementioned tetrahydroimidazo[1,2-h][1,7]naphthyridines are described in the examples.

The compounds of the formula 2 are known or may be prepared starting from appropriate starting compounds using similar process steps (see, for example, WO 01/72756, scheme 2 where G=hydrogen) as described exemplarily in the examples which follow herein below.

The examples which follow serve to illustrate the invention without limiting it. Equally, further compounds of the formula 1 whose preparation is not explicitly described may be prepared in a similar manner or a manner familiar to those skilled in the art using customary process techniques. The abbreviation min represents minute(s), h represents hour(s) and m.p. represents melting point.

EXAMPLES

End Products of the Formula I 1. rac-7-Acetoxy-10-acetyl-2,3-dimethyl-9-phenyl-9,10-dihydroimidazo[1,2-h][1,7]naphthyridine 90.0 g (0.31 mol) of rac-2,3-dimethyl-9-phenyl-7,8,9,10-tetrahydroimidazo[1,2-h][1,7]naphthyridine-7-one are suspended in 250 ml of acetic anhydride and admixed with 20 ml of methanesulphonic acid. The mixture is then heated to reflux for 3 h. After cooling, the acetic anhydride is distilled off under reduced pressure and the oily residue is added to 200 ml of water. The pH of the mixture is adjusted to pH 9 by adding concentrated ammonia solution with stirring. After adding 200 ml of water, extraction is effected using methylene chloride. The organic phase is washed with water, dried over magnesium sulphate and evaporated. The residue is crystallized using diethyl ether, and the precipitate is filtered off with suction and washed with diethyl ether. 85.4 g (74%) of the title compound are isolated as a yellow solid (m.p. 237-239° C.).

2. (9S)-7-Acetoxy-10-acetyl-2,3-dimethyl-9-phenyl-9,10-dihydroimidazo[1,2-h][1,7]naphthyridine 8.7 g (0.03 mol) of (9S)-2,3-dimethyl-9-phenyl-7,8,9,10-tetrahydroimidazo[1,2-h][1,7]naphthyridine-7-one are suspended in 49 ml of acetic anhydride, admixed with 2 ml of methanesulphonic acid and heated to reflux. After 30 min, another 2 ml of methanesulphonic acid are added. After 1 h, the reaction mixture is added to 250 ml of ice-water and neutralized by adding concentrated ammonia solution. Extraction is effected using methylene chloride, and the organic phase is dried over magnesium sulphate and evaporated. The residue is crystallized using diethyl ether, and the precipitate is filtered off with suction and washed with diethyl ether. 7.2 g (65%) of the title compound are isolated as a yellow solid (m.p. 237-239° C.).

3. rel-(7S,9S)-10-Acetyl-7-hydroxy-2,3-dimethyl-9-phenyl-7,8,9,10-tetrahydroimidazo[1,2h][1,7]-naphthyridine (racemic)

12.2 g (32.5 mmol) of rac-7-acetoxy-10-acetyl-2,3-dimethyl-9-phenyl-9,10-dihydroimidazo[1,2-h][1,7]-naphthyridine are dissolved in 50 ml of methanol and 10 ml of dichloromethane. 5.0 g (132 mmol) of sodium borohydride are then introduced at 0° C. over a period of 2 h. After 3 h, 30 ml of saturated ammonium chloride solution are added. The reaction mixture is extracted using dichloromethane, and the organic phase is dried over magnesium sulphate and evaporated. The residue is crystallized using diethyl ether. 8.2 g (75%) of the title compound are isolated as a colorless solid (m.p. 217° C.).

4. rac-10-Acetyl-2,3-dimethyl-9-phenyl-9,10-dihydroimidazo[1,2-h][1,7]naphthyridine (racemic)

6.0 g (17.9 mmol) of rel-(7S,9S)-10-acetyl-7-hydroxy-2,3-dimethyl-9-phenyl-7,8,9,10-tetrahydroimidazo[1,2-h][1,7]naphthyridine (racemic) are dissolved in 100 ml of dichloromethane and 20 ml of triethylamine. A solution of 2.9 g (25 mmol) of methanesulphonyl chloride in 5 ml of dichloromethane is then added dropwise with ice cooling within 30 min. After 2 h, hydrolysis is effected using water and extraction using dichloromethane. The organic phase is dried over magnesium sulphate and evaporated. The residue is crystallized using diethyl ether. 4.8 g (85%) of the title compound are isolated as a pale brown solid (m.p. 170° C.).

Use of Compounds of the Formula 1 According to the Invention for Preparing Active Ingredients Having a Tetrahydroimidazo[1.2-h][1,7]naphthyridine Structure

A. (8R,9R)-10-Acetyl-8-hydroxy-2,3-dimethyl-9-phenyl-7,8,9,10-tetrahydroimidazo[1,2-h][1,7]-naphthyridin-7-one 2.0 g (5.4 mmol) of (9S)-7-acetoxy-10-acetyl-2,3-dimethyl-9-phenyl-9,10-dihydroimidazo[1,2h][1,7]-naphthyridine are dissolved in 30 ml of acetone and 6 ml of water. 1.0 g (6.4 mmol) of potassium permanganate is then introduced in portions at 0° C. After 30 min, the brown suspension is admixed with 1 ml of saturated sodium hydrogensulphite solution, filtered through Celite and washed with methanol and dichloromethane. The filtrate is concentrated and the residue crystallized using ethanol. 0.3 g (16%) of the title compound is isolated as a yellow solid (m.p. 192° C.).

B. (7R,8R,9R)-10-Acetyl-7,8-dihydroxy-2,3-dimethyl-9-phenyl-7,8,9,10-tetrahydroimidazo[1,2-h][1,7]naphthyridine 0.2 g (0.6 mmol) of (8R,9R)-10-acetyl-8-hydroxy-2,3-dimethyl-9-phenyl-7,8,9,10-tetrahydroimidazo[1,2-h][1,7]naphthyridin-7-one is dissolved in 15 ml of methanol and admixed with 40 mg (1.1 mmol) of sodium borohydride in portions with ice cooling. After 10 min, hydrolysis is effected using saturated sodium hydrogencarbonate solution and extraction using dichloromethane. The organic phase is dried over magnesium sulphate and evaporated. The residue is crystallized using diethyl ether. 0.16 g (80%) of the title compound is isolated as a colourless solid (m.p. 260-261° C.).

C. (7R,8R,9R)-7,8-Dihydroxy-2,3-dimethyl-9-phenyl-7,8,9,10-tetrahydroimidazo[1,2-h][1,7]-naphthyridine The N-acetyl protecting group is detached from the compound (7R,8R,9R)-10-acetyl-7,8-dihydroxy-2,3-dimethyl-9-phenyl-7,8,9,10-tetrahydroimidazo[1,2-h][1,7]naphthyridine by heating with potassium carbonate in 2-aminoethanol (temp. 70-100° C.). After extractive workup and crystallization, the title compound is obtained as a colourless solid of m.p. 206-209° C.

Starting Compounds

AA. (9S)-2,3-Dimethyl-9-phenyl-5,6,7,8,9,10-hexahydroimidazo[1,2-h][1,7]naphthyridin-7-one 9.7 g (51.6 mmol) of ethyl (S)-3-amino-3-phenylpropionate, 8.5 g (51.6 mmol) of 2,3-dimethyl-6,7-dihydro-5H-imidazo[1,2-a]pyridin-8-one and 0.26 g (1.3 mmol) of p-toluenesulphonic acid monohydrate are heated to reflux in 50 ml of toluene using a water separator. After no more water separates, the reaction mixture is cooled to 0° C. and diluted with 100 ml of tetrahydrofuran. 7.24 g (64.5 mmol) of potassium tert-butoxide are then introduced and the mixture is stirred at room temperature for 16 h. 150 ml of saturated ammonium chloride are added to the reaction mixture, the organic phase is removed and the aqueous phase is extracted with 300 ml of ethyl acetate. The combined organic phases are washed with 250 ml of water, dried over sodium sulphate and evaporated. 13.27 g (88%) of the title compound are isolated as a red-brown oil. An analytical sample is obtained by crystallizing with diethyl ether (red solid, m.p. 134° C.).

BB. (9S)-2,3-Dimethyl-9-phenyl-7,8,9,10-tetrahydroimidazo[1,2-h][1,7]naphthyridin-7-one 63.5 g (0.22 mol) of (9S)-2,3-dimethyl-9-phenyl-5,6,7,8,9,10-hexahydroimidazo[1,2-h][1,7]naphthyridin-7-one are dissolved in 250 ml of toluene and 250 ml of tetrahydrofuran, and cooled to 0° C. 59 g (0.26 mol) of 2,3-dichloro-5,6-dicyano-1,4-benzoquinone are introduced in portions of 10 g over a period of 1 h with mechanical stirring. The reaction mixture is stirred at room temperature for 16 h. 1.2 l of 0.5 N sodium hydroxide solution and 1 l of ethyl acetate are then added dropwise. The organic phase is removed and washed with water. The aqueous phase is reextracted with ethyl acetate, and the combined organic phases are dried over sodium sulphate and evaporated. The residue is crystallized at 0° C. in 300 ml of methanol. The solid is filtered off with suction, washed with cold methanol and dried. 20 g (32%) of the title compound are isolated as a pale yellow solid (m.p. 103-105° C.).

COMMERCIAL APPLICABILITY

The compounds of the formula 1 and their salts are valuable intermediates for preparing active ingredients, as disclosed, for example, in the International Patent Applications WO 98/42707, WO 00/17200, WO 00/26217, WO 00/63211, WO 01/72756, WO 01/72754, WO 01/72757 and WO 02/34749.

The invention claimed is:

1. A compound of the formula 1**

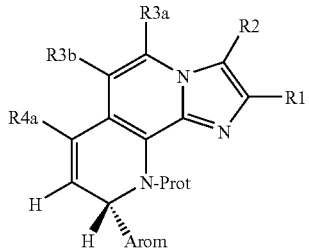
(1**)

where
R1 is hydrogen, methyl, cyclopropyl, methoxymethyl or trifluoromethyl,
R2 is hydrogen, methyl, chlorine, bromine, ethynyl or trifluoromethyl,
R3a is hydrogen,
R3b is hydrogen, fluorine, methyl or the —CO—N(CH$_3$)$_2$ radical,
R4a is R41-O,
Arom is a phenyl radical,
Prot is R41 and
R41 is selected from the group consisting of C$_{1-4}$-alkyl-carbonyl, C$_{1-4}$-alkoxycarbonyl and C$_{1-4}$-alkoxy-C$_{1-4}$-alkoxycarbonyl,
or a salt thereof.

2. A compound of the formula 1** according to claim 1, where
R1 is methyl,
R2 is methyl,
R3a is hydrogen,
R3b is hydrogen,
R4a is R41-O,
Arom is a phenyl radical,
Prot is R41 and
R41 is selected from the group consisting of C$_{1-4}$-alkyl-carbonyl, C$_{1-4}$-alkoxycarbonyl and C$_{1-4}$-alkoxy-C$_{1-4}$-alkoxycarbonyl,
or a salt thereof.

3. A compound of the formula 1** according to claim 1, where R41 is acetyl.

4. A compound of the formula 1** according to claim 2, where R41 is acetyl.

* * * * *